United States Patent
Woodward et al.

(10) Patent No.: US 6,403,649 B1
(45) Date of Patent: *Jun. 11, 2002

(54) NON-ACIDIC CYCLOPENTANE HEPTANOIC ACID,2-CYCLOALKYL OR ARYLALKYL DERIVATIVES AS THERAPEUTIC AGENTS

(75) Inventors: David F. Woodward, El Toro; Steven W. Andrews, Rancho Santa Marguerita; Robert M. Burk, Irvine; Michael E. Garst, Newport Beach, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/519,834

(22) Filed: Mar. 6, 2000

Related U.S. Application Data

(60) Continuation of application No. 08/876,937, filed on Jun. 16, 1997, which is a continuation of application No. 08/605,567, filed on Feb. 22, 1996, now Pat. No. 5,688,819, which is a continuation-in-part of application No. 08/371,339, filed on Jan. 11, 1995, now Pat. No. 5,607,978, which is a continuation of application No. 08/154,244, filed on Nov. 18, 1993, now abandoned, which is a division of application No. 07/948,056, filed on Sep. 21, 1992, now Pat. No. 5,352,708.

(51) Int. Cl.⁷ ............................................. A61K 31/135
(52) U.S. Cl. ..................... 514/646; 564/171; 564/189
(58) Field of Search .............................. 514/530, 546, 514/548, 555, 570, 913, 646; 560/53, 60, 255; 562/452, 465; 564/171, 189

(56) References Cited

U.S. PATENT DOCUMENTS

| 4,055,602 A | 10/1977 | Nelson |
|---|---|---|
| 4,097,489 A | 6/1978 | Bundy |
| 4,128,713 A | 12/1978 | Schneider |
| 4,131,738 A | 12/1978 | Smith |
| 4,171,331 A | 10/1979 | Biddlecom et al. |
| 4,183,870 A | 1/1980 | Caton et al. |
| 4,444,788 A | 4/1984 | Skuballa et al. |
| 4,599,353 A | 7/1986 | Bito |
| 4,994,274 A | 2/1991 | Chan et al. |
| 5,034,413 A | 7/1991 | Chan et al. |
| 5,352,708 A | 10/1994 | Woodward et al. |
| 5,414,016 A | 5/1995 | Skuballa et al. |
| 5,510,383 A | 4/1996 | Bishop et al. |
| 5,545,665 A | 8/1996 | Burk |
| 5,587,391 A | 12/1996 | Burk |
| 5,607,978 A | 3/1997 | Woodward et al. |

FOREIGN PATENT DOCUMENTS

| CA | 2036386 | 1/1991 |
|---|---|---|
| CS | 271137 | * 8/1990 |
| DE | 27 21 534 | 12/1977 |
| EP | 0 093 380 | 11/1983 |
| EP | 0 102 230 | 7/1984 |
| EP | 0 253 094 | 1/1988 |
| EP | 0 364 417 | 1/1989 |
| EP | 0 453 127 | 10/1991 |
| FR | 2 312 240 | 12/1976 |
| FR | 2 386 523 | 11/1978 |
| FR | 2 402 644 | 3/1979 |
| LU | 68 940 | 2/1974 |
| WO | 90/02553 | 3/1990 |
| WO | 92/08465 | 5/1992 |

OTHER PUBLICATIONS

Prostaglandins: vol. 13, No. 5, May 1977, Stoneham, MA, pp. 837–843, H.C. Arndt, "The Synthesis and Biological Activity of Prostaglandins Analogs Containing Spiroocyclic Rings".

Tetrahedron: Vo. 32, 1976, Oxford GB, pp. 2747–2752, P. De Clercqet al, "Cyclopentanones–XV1,. Prostaglandin Synthesis Involving Catalytic Hydrogenation of 2,3–Dialkyl–4–Hydroxy–2–Cyclopentenones".

Derwent Pub. Lts. London GB AN 71–57225 & JP A, 46 030 830, Ono Pharmaceutical Co., Sep. 7, 1971.

Bito, L.Z., "Prostaglandins and Related Compounds as Potential Ocular Therapeutic Agents", Biological Protection with Prostaglandins (Cohen, M.M., ed., Boc Raton, FL, CRC Press Inc., 1985, pp. 231–252.

Bito,L.Z., "Prostaglandins, Old Concepts and New Perspectives," Arch Oph., vol. 105, Aug. 1987 p. 1036–1039.

Starr, M.S., "Further Studies on the Effect of Prostaglandin on Intraocular Pressure in the Rabbit", Exp. Eye Res., (1971) 170–177.

Nilsson, Siv F.E., et al, "PGF2a Increases Uveoscleral Outflow", ARVO Abstract, p. 284, Invest. Ophthalmol. Vis. Sic. 28 (suppl) (1987).

Bito, L.Z., "Prostaglandins, Other Eicosanoids, and Their Derivatives as Potential Antiglaucoma Agents", Applied Pharmacology in the Medical Treatment of Glaucoma, pp. 477–505, 1984.

* cited by examiner

*Primary Examiner*—Sreeni Padmanabhan
(74) *Attorney, Agent, or Firm*—Robert J. Baran; Martin A. Voet; Carlos A. Fisher

(57) ABSTRACT

The present invention provides cydopentane heptanoic acid, 2-cycloalkyl or arylalkyl compounds, which may be substituted in the 1-position with amino, amido, ether or ester groups, e.g., a 1-OH cydopentane heptanoic acid, 2-(cycloalkyl or arylalkyl) compound. The cydopentane heptanoic acid, 2-(cycloalkyl or arylalkyl) compounds of the present invention are potent ocular hypotensives, and are particularly suitable for the management of glaucoma. Moreover, the cydopentane heptanoic, 2-(cycloalkyl or arylalkyl) compounds of this invention are smooth muscle relaxants with broad application in systemic hypertensive and pulmonary diseases; smooth muscle relaxants with application in gastrointestinal disease, reproduction, fertility, incontinence, shock, etc.

3 Claims, No Drawings

NON-ACIDIC CYCLOPENTANE HEPTANOIC ACID,2-CYCLOALKYL OR ARYLALKYL DERIVATIVES AS THERAPEUTIC AGENTS

CROSS-REFERENCE TO RELATED APPLICATIONS

This patent application is a continuation of U.S. patent application Ser. No. 08/876,937 filed Jun. 16, 1997, which is a continuation of U.S. patent application Ser. No. 08/605,567, filed Feb. 22, 1997, now U.S. Pat. No. 5,688,819, which is a continuation-in-part of U.S. patent application Ser. No. 08/371,339, filed on Jan. 11, 1995 now U.S. Pat. No. 5,607,978 which is a continuation of U.S. patent application Ser. No. 08/154,244 which was filed on Nov. 18, 1993, now ABN which is a divisional of U.S. patent application Ser. No. 07/948,056, filed on Sep. 21, 1992, now U.S. Pat. No. 5,352,708 issued on Oct. 4, 1994, all of which are hereby incorporated by reference.

BACKGROUND OF THE INVENTION

1. Field of the Invention

The present invention provides cyclopentane heptanoic acid, 2-cycloalkyl or arylalkyl compounds, which may be substituted in the 1-position with amino, amido, ether or ester groups, e.g., a 1-OH cydopentane heptanoic acid, 2-(cycloalkyl or arylalkyl) compound. The cydopentane heptanoic acid, 2-(cycloalkyl or arylalkyl) compounds of the present invention are potent ocular hypotensives, and are particularly suitable for the management of glaucoma. Moreover, the cydopentane heptanoic, 2-(cycloalkyl or arylalkyl) compounds of this invention are smooth muscle relaxants with broad application in systemic hypertensive and pulmonary diseases; smooth muscle relaxants with application in gastrointestinal disease, reproduction, fertility, incontinence, shock, etc.

2. Description of the Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. *Exp. Eye Res.* 1971, 11, pp. 170–177; Bito, L. Z. *Biological Protection with Prostaglandins* Cohen, M. M., ed., Boca Raton, Fla. CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2a}$, $PGF_{1a}$, $PGE_2$, and certain lipid-soluble esters, such as $C_1$ to $C_5$ alkyl esters, e.g. 1-isopropyl ester, of such compounds.

In the U. S. Pat. No. 4,599,353 certain prostaglandins, in particular PGE2 and $PGF_{2a}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28(suppl), 284 (1987)].

The isopropyl ester of $PGF_{2a}$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch. Ophthalmol.* 105 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2a}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2a}$. Intraocular pressure reducing 15-acyl prostaglandins are disclosed in the co-pending application U.S. Ser. No. 357,394 (filed May 25, 1989). Similarly, 11,15- 9,15-and 9,11-diesters of prostaglandins, for example 11,15-dipivaloyl $PGF_{2a}$ are known to have ocular hypotensive activity. See the co-pending patent applications U.S. Ser. No. 385,645 filed Jul. 27, 1990, now U.S. Pat. Nos. 4,494,274; 584,370 which is a continuation of U.S. Ser. Nos. 386,312, and 585,284, now U.S. Pat. No. 5,034,413 which is a continuation of U.S. Ser. No. 386,834, where the parent applications were filed on Jul. 27, 1989. The disclosures of these patent applications are hereby expressly incorporated by reference.

SUMMARY OF THE INVENTION

We have found that certain cyclopentane heptanoic acid, 2-cycloalkyl or arylalkyl compounds and derivatives thereof wherein the carboxylic acid group is replaced by a non-acidic substituent have pronounced effects on smooth muscle and are potent ocular hypotensive agents. We have further found that such compounds, in certain instances, may be significantly more potent than their respective parent compounds and, in the case of glaucoma surprisingly, cause no or significantly lower ocular surface hyperemia than the parent compounds.

The present invention relates to methods of treating cardiovascular, pulmonary-respiratory, gastrointestinal, reproductive, allergic disease, shock and ocular hypertension which comprises administering an effective amount of a cyclopentane heptanoic acid, 2-cycloalkyl or arylalkyl compound represented by the formula I

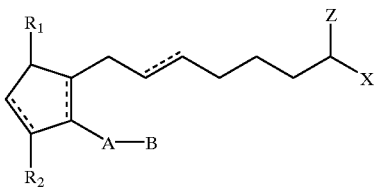

wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or akylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is a radical selected from the group consisting of —$OR^4$ and —$N(R^4)_2$ wherein $R^4$ is selected from the group consisting of hydrogen, a lower alkyl radical having from one to six carbon atoms,

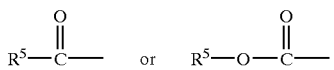

wherein $R^5$ is a lower alkyl radical having from one to six carbon atoms; Z is =O or represents 2 hydrogen radicals; one of $R_1$ and $R_2$ is =O, —OH or a —$O(CO)R^6$ group, and the other one is —OH or —$O(CO)R^6$, or $R_1$ is =O and $R_2$ is H, wherein $R_6$ is a saturated or unsaturated acyclic hydrocarbon group having from 1 to about 20 carbon atoms, or —$(CH_2)mR_7$ wherein m is 0 or an integer of from 1 to 10, and $R_7$ is cycloalkyl radical, having from three to seven carbon atoms, or a hydrocarbyl aryl or heteroaryl radical, as defined above, or a pharmaceutically-acceptable salt thereof, provided, however, that when B is not substituted with a pendant heteroatom-containing radical, and Z is =O, then X is not —$OR^4$. (That is, the cycloalkyl or hydrocarbyl aryl or heteroaryl radical is not substituted with a pendant radical having an atom other than carbon or hydrogen.)

More preferably the method of the present invention comprises administering a cyclopentane heptanoic acid, 2-(phenyl alkyl or phenyloxyalkyl) represented by the formula II

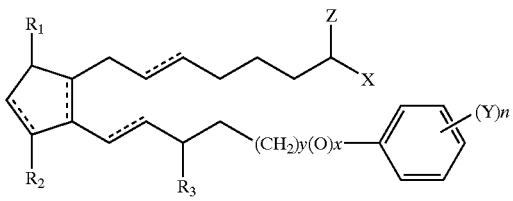

wherein y is 0 or 1, x is 0 or 1 and x and y are not both 1, Y is a radical selected from the group consisting of alkyl, halo, e.g. fluoro, chloro, etc., nitro, amino, thiol, hydroxy, alkyloxy, alkylcarboxy, halo substituted alkyl wherein said alkyl radical comprises from one to six carbon atoms, etc. and n is 0 or an integer of from 1 to about 3 and $R_3$ is =O, —OH or —$O(CO)R_6$ wherein $R_6$ is as defined above. Preferably, n is 1 or2.

Preferably the compound used in the above method of treatment is a compound of formula (III).

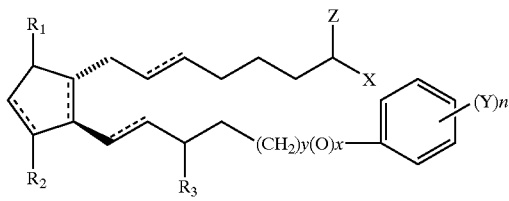

wherein hatched lines indicate a configuration, solid triangles are used to indicate β configuration In another aspect, the present invention relates to a method of treating cardiovascular, pulmonary-respiratory, gastrointestinal, reproductive and allergic diseases, shock and ocular hypertension which comprises administering to a subject a pharmaceutical composition comprising a therapeutically effective amount of a compound of formula (IV)

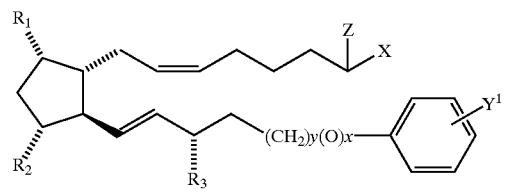

wherein $Y^1$ is Cl or trifluoromethyl and the other symbols and substituents are as defined above, in combination with a pharmaceutical carrier.

Finally, the method of the present invention relates to a method of treating cardiovascular, pulmonary-respiratory, gastrointestinal, reproductive and allergic diseases, shock and ocular hypertension which comprises administering to a subject a pharmaceutical composition comprising a therapeutically effective amount of a compound of Formula V

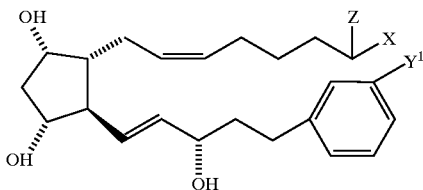

and the 9-and/or 11-and/or 15 esters thereof.

In a further aspect, the present invention relates to pharmaceutical compositions comprising a therapeutically effective amount of a compound of formulae (I), (II), (III), (IV) or (V) wherein the symbols have the above meanings, or a pharmaceutically acceptable salt thereof in admixture with a non-toxic, pharmaceutically acceptable liquid vehicle.

In a still further aspect, the present invention relates to cyclopentane heptanoic acid, 2-cycloalkyl or arylalkyl compounds of the above formulae, wherein the substituents and symbols are as defined hereinabove, or a pharmaceutically acceptable salt of such compounds.

DETAILED DESCRIPTION OF THE INVENTION

The present invention relates to the use of cyclopentane heptanoic acid, 2-cycloalkyl or arylalkyl compounds as therapeutic agents, e.g. as ocular hypotensives. These therapeutic agents are represented by compounds having the formula I,

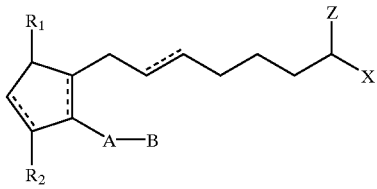

as defined above. The preferred nonacidic cyclopentane heptanoic acid, 2-(phenyl alkyl or phenyloxyalkyl) compounds used in accordance with the present invention are encompassed by the following structural formula (II)

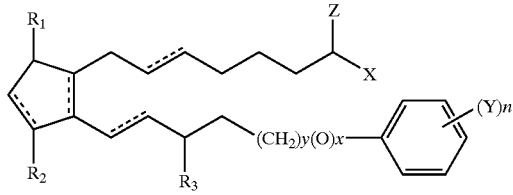

wherein the substituents and symbols are as hereinabove defined. More preferably the compounds are represented by formula (III).

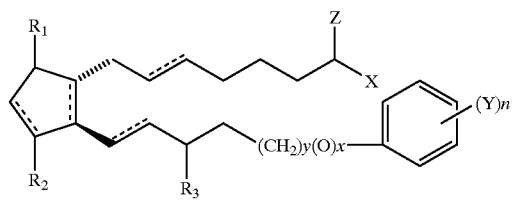

wherein the substituents and symbols are as defined above. More preferably, the compounds utilized in the present invention are compounds represented by the formula (IV)

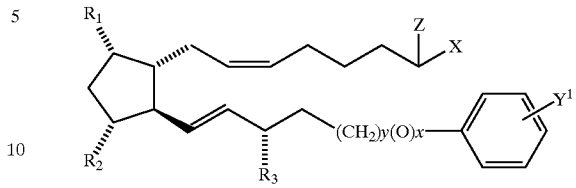

wherein the substituents and the symbols are as defined above.

Most preferably the present invention utilizes the novel compounds of the formula (V)

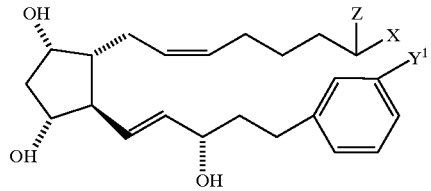

and their 9-and/or 11-and/or 15-esters.

In all of the above formulae, as well as in those provided hereinafter, the dotted lines on bonds between carbons 5 and 6 (C-5), between carbons 13 and 14 (C-13), between carbons 8 and 12 (C-8), and between carbons 10 and 11 (C-10) indicate a single or a double bond which can be in the cis or trans configuration. If two solid lines are used that indicates a specific configuration for that double bond. Hatched lines at positions C-9, C-11 and C-15 indicate the α configuration. If one were to draw the β configuration, a solid triangular line would be used.

In the compounds used in accordance with the present invention, compounds having the C-9 or C-11 or C-15 substituents in the α or β configuration are contemplated. As hereinabove mentioned, in all formulas provided herein broken line attachments to the cydopentane ring indicate substituents in the a configuration. Thickened solid line attachments to the cyclopentane ring indicate substituents in the β configuration. Also, the broken line attachment of the hydroxyl group or other substituent to the C-11 and C-15 carbon atoms signifies the α configuration.

For the purpose of this invention, unless further limited, the term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about 6, preferably one to about 4 carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

The definition of $R_6$ may include a cyclic component, —$(CH_2)_m R_7$, wherein n is 0 or an integer of from 1 to 10, $R_7$ is an aliphatic ring from about 3 to about 7 carbon atoms, or an aromatic or heteroaromatic ring. The "aliphatic ring" may be saturated or unsaturated, and preferably is a saturated ring having 3–7 carbon atoms, inclusive. As an aromatic ring, $R_7$ preferably is phenyl, and the heteroaromatic rings have oxygen, nitrogen or sulfur as a heteroatom, i.e. $R_7$ may be thienyl, furanyl, pyridyl, etc. Preferably m is 0 or an integer of from 1 to 4.

Z is =O or represents two hydrogen atoms.

X may be selected from the group consisting of —OR$^4$ and —N(R$^4$)$_2$ wherein R$^4$ is selected from the group consisting of hydrogen, a lower alkyl radical having from one to six carbon atoms,

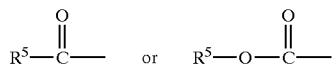

wherein R$^5$ is a lower alkyl radical having from one to six carbon atoms.

Preferred representatives of the compounds within the scope of the present invention are the compounds of formula V wherein X is —OH, i.e. cyclopentane heptenoic acid, 5-cis-2-(3-αhydroxy-4-m-chlorophenoxy-1-trans-butenyl) 3,5-dihydroxy, [1$_α$, 2$_β$, 3$_α$, 5$_α$] and cyclopentane methylheptenoate-5-cis-2(3-αhydroxy-4m-chlorophenoxy-1-trans-butenyl)-3,5 dihydroxy, [1$_α$, 2$_β$, 3$_α$, 5$_α$] 1 and the 9- and/or 11- and/or 15-esters of this compound. (The numbered designations in brackets refer to the positions on the cyclopentane ring.)

The following novel compounds may be used in the a pharmaceutical compositions and the methods of treatment of the present invention.

(1) cyclopentane heptenol-5cis-2-(3α-hydroxy-5-phenyl-1-trans-pentenyl)-3,5-dihydroxy, [1$_α$, 2$_β$, 3$_α$, 5$_α$]

(2) cydopentane heptenamide-5-cis-2-(3α-hydroxy-5phenyl-1-trans-pentenyl)-3,5-dihydroxy, [1$_α$, 2$_β$, 3$_α$5$_α$]

(3) cydopentane N,N-dimethylheptenamide-5-cis-2-(3α-hydroxy-5-phenyl-1-trans-pentenyl-3,5-dihydroxy, [1$_α$, 2$_β$, 3$_α$, 5$_α$]

(4) cydopentane heptenyl methoxide-5-cis-2-(3α-hydroxy-5-phenyl-1-trans-pentenyl)-3,5dihydroxy, [1$_α$, 2$_β$, 3$_α$, 5$_α$]

(5) cyclopentane heptenyl ethoxide-5-cis-2-(3α-hydroxy-4-meta-chlorophenoxy-1-trans-pentenyl)-3,5-dihydroxy, [1$_α$, 2$_β$, 3$_α$, 5$_α$]

(6) cyclopentane heptenylamide-5-cis-2-(3α-hydroxy-4-meta-chlorophenoxy-1-trans-pentenyl)-3,5-dihydroxy, [1$_α$, 2$_β$, 3$_α$, 5$_α$]

(7) cydopentane heptenylamide-5cis-2-(3α-hydroxy-4-trifluoromethylphenoxy-1-trans-pentenyl)-3, 5dihydroxy, [1$_α$, 2$_β$, 3$_α$, 5$_α$]

(8) cyclopentane N-isopropyl heptenamide-5-cis-2-(3α-hydroxy-5phenyl-1-trans-pentenyl)-3,5-dihydroxy, [1$_α$, 2$_β$, 3$_α$, 5$_α$]

(9) cydopentane N-ethyl heptenamide-5-cis-2-(3α-hydroxy-5-phenyl-1-trans-pentenyl)-3,5 dihydroxy, [1$_α$, 2$_β$, 3$_α$, 5$_α$]

(10) cyclopentane N-methyl heptenamide-5-cis-2-(3α-hydroxy-5-phenyl-1-trans-pentenyl)-3,5-dihydroxy, [1$_α$, 2$_β$, 3$_α$, 5$_α$]

(11) cyclopentane heptenol-5-cis-2-(3α-hydroxy-4-meta-chlorophenoxy-1-trans-butenyl)-3,5 -dihydroxy, [1$_α$, 2$_β$, 3$_α$, 5$_α$]

(12) cydopentane heptenamide-5-cis-2-(3α-hydroxy-4-meta-chlorophenoxy-1-trans-butenyl)-3,5-dihydroxy, [1$_α$, 2$_β$, 3$_α$, 5$_α$]

(13) cydopentane heptenol-5-cis-2-(3α-hydroxy-5phenyl-1-trans-pentenyl)3,5 -dihydroxy, [1$_α$, 2$_β$, 3$_α$, 5$_α$]

A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/y) |
| --- | --- |
| active ingredient | about 0.001–5 |
| preservative | 0–0.10 |
| vehicle | 0–40 |
| tonicity adjustor | 0–10 |
| buffer | 0.01–10 |

-continued

| Ingredient | Amount (% w/y) |
| --- | --- |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 ml.

The invention is further illustrated by the following non-limiting Examples.

EXAMPLE 1

Cyclopentane heptenoic acid, 5-cis-2-(3α-hydroxy-4m-chlorophenoxy-1-trans-butenyl)-3,5-dihydroxy
$[1_\alpha, 2_\beta, 3_\alpha, 5_\alpha]$ This compound may be purchased from Cayman Chemical Company of Ann Arbor, Mich. or synthesized by methods known in the art.

EXAMPLE 2

Cyclopentane methylheptenoate-5-cis-2(3α-hydroxy-4-m-chlorophenoxy-1-trans butenyl) -3,5-dihydroxy, $[1_\alpha, 2_\beta, 3_\alpha, 5_\alpha]$ To a stirred solution of cyclopentane heptenoic acid, 5-cis-2-(3α-hydroxy-4-m-chlorophenoxy-1-trans-butenyl)-3,5-dihydroxy, $[1_\alpha, 2_\beta, 3_\alpha, 5_\alpha]$(24 mg. 0.0565 mmol) in acetone (0.6 ml) at room temperature was added 1,8-diazabicyclo [5.4.0.] undec-7-ene (DBU) (40, ul, 0.27 mmol) and methyl iodide (20 ul, 0.32 mmol). The reaction turned yellow with the DBU addition. The reaction was maintained at room temperature for 6.5 hours, then was diluted with ethyl acetate (30 ml) and filtered through a plug of celite with the aid of ethyl acetate. After concentration in vacuo, the residue was flushed with ethylacetate (EtOAc) through a 20 mm×160 mm column of silica to give the desired methyl ester.

EXAMPLE 3

Cyclopentane heptenamide-5-cis-2-(3α-hydroxy-4-m-chlorophenoxy-1-trans-butenyl) -3,5-dihydroxy, $[1_\alpha, 2_\beta, 3_\alpha, 5_\alpha]$ A mixture of the methyl ester of the compound of Example 1 (9.2 mg, 0.0222 mmol) and $NH_4Cl$ (10 mg, 0.187 mmol) in $NH_3$ was heated at 80° C. for 12 hours. After cooling to room temperature, the solvents were evaporated and the residue was subjected to column chromatography to provide the named amide as 7.2 mg of a dear, colorless liquid.

EXAMPLE 4

Cyclopentane heptenoic acid-5-cis2-(3α-hydroxyl-4-m-trifluoromethylphenoxy-1-trans-butenyl)-3,5-dihydroxy $[1_\alpha, 2_\beta, 3_\alpha, 5_\alpha]$ This compound may be purchased from Cayman Chemical Company of Ann Arbor, Mich. or synthesized by methods known in the art.

EXAMPLE 5

Cydopentane heptenamide-5-cis2-(3α-hydroxy-4-m-trifluoromethylphenoxy-1-trans-butenyl)-3,5-dihydroxy $[1_\alpha, 2_\beta, 3_\alpha, 5_\alpha]$ A mixture of the methyl ester of the compound of Example 4 (fluprostenol) and $NH_4Cl$ in $NH_3$ is heated at 80° C. for 12 hours. After cooling to room temperature the solvents are evaporated and the residue is subjected to column chromatography to provide the named amide.

EXAMPLE 6

Measurement of intraocular pressure studies in dogs involved pneumatonometry performed in conscious, Beagle dogs of both sexes (10–15 kg). The animals remained conscious throughout the study and were gently restrained by hand. Drugs were administered topically to one eye as a 25 $\mu L$ volume drop, the other eye received 25$\mu$: vehicle (0.1% polysorbate 80:10 mM TRIS) as a control. 0.1% proparacaine was used for corneal anesthesia during tonometry. Intraocular pressure was determined just before drug administration and at 2, 4 and 6 hour thereafter on each day of the 5 day study. Drug was administered twice a day, with a 6 hour interval between doses that spanned the intraocular pressure measurement time frame. The result reported in Table 1, below.

TABLE 1

Comparison of effects of certain compounds of the invention on dog intraocular pressure. Values indicate mean changes from baseline introcular pressure (± SEM) at predetermined times post-dosing. n = 8, *p < 0.05, **p < 0.01.
INTRAOCULAR PRESSURE (mmHg) CHANGE AT PREDETERMINED TIMES (HR)

| COMPOUND | DOSE % | 2 | 4 | 6 | 24 |
| --- | --- | --- | --- | --- | --- |
| Example 1 | 0.01 | −0.1 ± 0.8 | −5.2 ± 1.4** | −4.3 ± 0.8 | −4.4 ± 0.8 |
| Example 1 | 0.1 | −3.1 ± 0.8** | −3.2 ± 0.7 | −2.7 ± 0.8 | — |
| Example 3 | 0.01 | −2.2 ± 1.0* | 5.5 ± 1.1** | −4.0 ± 1.4* | 2.7 ± 1.1* |
| Example 3 | 0.1 | −1.3 ± 0.4* | 2.3 ± 0.7** | −2.6 ± 0.6** | — |
| Example 5 | 0.1 | −2.7 ± 0.8* | −3.4 ± 0.9* | −2.8 ± 0.4** | −2.1 ± 1.6* |
| Example 4 | 0.01 | −0.9 ± 0.7 | −2.5 ± 0.7* | −3.2 ± 0.7** | −1.3 ± 0.7 |
| Fluprostenol | 0.1 | −1.3 ± 0.1 | −2.1 ± 1.1 | −2.7 ± 1.3 | −3.1 ± 0.9* |

EXAMPLE 7

Measurement of ocular surface hyperemia was visually assessed and scored according to the following schematic:

| Hyperemia Score | Assigned Value |
| --- | --- |
| <1 | 1 |
| 1 slight | 2 |
| >1<2 | 3 |
| 2 moderate | 4 |
| >2>3 | 5 |
| 3 severe | 6 |

(baseline scores for dogs are typically < 1)

The hyperemia value for each dog at a single time point (x) is obtained as follows: (treated eye value at hr x-baseline value)-(control eye value at hr x-baseline value). A composite value is then obtained by dividing the sum of the post-treatment measurement at each time point by the number of animals in the group: i.e. m where m=n measurements of ocular surface hyperemia. Ocular surface hyperemia is evaluated at the same time points as intraocular pressure measurement. It should be noted that untreated dog eyes frequently have a pink/red tone. Thus, values of <1 and 1 are essentially within the normal range. The results are reported in Table 2, below.

TABLE 2

Comparison of effects of certain compounds of the invention on dog ocular surface hyperemia. Values are composite scores as indicated in the methods.

| COMPOUND | DOSE % | OCULAR SURFACE HYPEREMIA: COMPOSITE SCORE |
| --- | --- | --- |
| Example 1 | 0.01 | — |
| Example 1 | 0.1 | 0.33 |
| Example 3 | 0.01 | — |
| Example 3 | 0.1 | 0.81 |
| Example 5 | 0.1 | 0.81 |
| Example 4 | 0.01 | 1.08 |
| Fluprostenol | 0.1 | 1.50 |

It is clear that the compounds of Examples 1, 3 and 5, unexpectedly, show better efficacy at lowering IOP than Example 4 while showing less hyperemia.

The compounds of the invention may also be useful in the treatment of various pathophysiological diseases including acute myocardial infarction, vascular thrombosis, hypertension, pulmonary hypertension, ischemic heart disease, congestive heat failure, and angina pectoris, in which case the compounds may be administered by any means that effect vasodilation and thereby relieve the symptoms of the disease. For example, administration may be by oral, transdermal, parenterial, subcutaneous, intravenous, intramuscular, intraperitoneal, transdermal, or buccal routes.

The compounds of the invention may be used alone, or in combination with other of the known vasodilator drugs.

The compounds of the invention may be formulated into an ointment containing about 0.10 to 10% of the active ingredient in a suitable base of, for example, white petrolatum, mineral oil and petroatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules make of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as inders such as starch, paste using for example, maize starch, wheat starch, rich starchy, potato starch, gelatin, tragacanth, methyl cellulose, hydroxypropylmethylcellulose, sodium carboxymethylcellulose, and/or polyvinyl pyrrplidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally containing gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tables or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, soribitol, and/or dextran. Optionally, the suspension may also contain stabilizers.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. For example, the present invention contemplates certain prodrugs of the above disclosed compounds, wherein

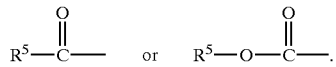

These compounds may be made by acylation or esterification of the corresponding hydroxy or amino derivative. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound, that is cyclopentane N-ethyl heptenamide-5-cis-2-(3α-hydroxy-5-phenyl-1-trans-pentenyl)-3,5-dihydroxy, [$1_\alpha$, $2_\beta$, $3_\alpha$, $5_\alpha$]).

2. A method of treating ocular hypertension which comprises applying to the eye an amount sufficient to treat ocular hypertension of the compound of claim 1.

3. A method of treating glaucoma which comprises applying to the eye an amount sufficient to treat glaucoma of the compound of claim 1.

* * * * *

UNITED STATES PATENT AND TRADEMARK OFFICE
CERTIFICATE OF CORRECTION

PATENT NO.   : 6,403,649 B1
DATED        : June 11, 2002
INVENTOR(S)  : Burk et al.

It is certified that error appears in the above-identified patent and that said Letters Patent is hereby corrected as shown below:

<u>Title page,</u>
Item [57], ABSTRACT,
Lines 1, 4, 5 and 9, delete "cydopentane" and insert in place thereof
-- cyclopentane --

<u>Column 1,</u>
Lines 26, 27 and 31, delete "cydopentane" and insert in place thereof
-- cyclopentane --

<u>Column 2,</u>
Line 28, delete "PGE2" and insert in place thereof -- $PGE_2$ --

<u>Column 6,</u>
Line 41, delete "cydopentane" and insert in place thereof -- cyclopentane --

<u>Column 7,</u>
Lines 26 and 44, delete "5cis" and insert in place thereof -- 5-cis --
Lines 28, 31, 35, 44, 50, 60 and 63, delete "cydopentane" and insert in place thereof -- cyclopentane --.
Lines 29, 48 and 64, "5phenyl" and insert in place thereof -- 5-phenyl --
Line 36, delete "3,5dihydroxy" and insert in place thereof -- 3,5-dihydroxy --
Line 46, delete "5dihydroxy" and insert in place thereof -- 5-dihydroxy --

<u>Column 8,</u>
Line 61, delete "w/y" and insert in place thereof -- w/v --

<u>Column 9,</u>
Line 4, delete "w/y" and insert in place thereof -- w/v --
Lines 33 and 61, delete "cydopentane" and insert in place thereof -- cyclopentane --

<u>Column 10,</u>
Line 3, delete "dear" to -- clear --
Line 16, delete "cydopentane" and insert in place thereof -- cyclopentane --

UNITED STATES PATENT AND TRADEMARK OFFICE
CERTIFICATE OF CORRECTION

PATENT NO. : 6,403,649 B1
DATED : June 11, 2002
INVENTOR(S) : Burk et al.

It is certified that error appears in the above-identified patent and that said Letters Patent is hereby corrected as shown below:

Column 13,
Line 2, after "wherein" insert -- $R_4$ is --

Signed and Sealed this

Twenty-ninth Day of October, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

| | | |
|---|---|---|
| PATENT NO. | : 6,403,649 B1 | |
| APPLICATION NO. | : 09/519834 | |
| DATED | : June 11, 2002 | |
| INVENTOR(S) | : Woodward et al. | |

It is certified that error appears in the above-identified patent and that said Letters Patent is hereby corrected as shown below:

On the Title page, in Item (54), in "Title", in column 1, line 2, delete "ACID,2-CYCLOALKYL" and insert -- ACID, 2-CYCLOALKYL --, therefor.

On the Title page, in Item (56), under "Other Publications", in column 2, line 3, delete "Spiroocyclic" and insert -- Spirocyclic --, therefor.

On the Title page, in Item (56), under "Other Publications", in column 2, line 5, delete "Vo. 32" and insert -- Vol. 32 --, therefor.

On the Title page, in Item (56), under "Other Publications", in column 2, line 6, delete "Clercqet al," and insert -- Clercqet et al. --, therefor.

On the Title page, in Item (56), under "Other Publications", in column 2, line 6, delete "Cyclopentanones-XV1,." and insert -- Cyclopentanones-XVI, --, therefor.

On the Title page, in Item (57), under "Abstract", in column 2, line 1, delete "cydopentane" and insert -- cyclopentane --, therefor.

On the Title page, in Item (57), under "Abstract", in column 2, line 4, delete "cydopentane" and insert -- cyclopentane --, therefor.

On the Title page, in Item (57), under "Abstract", in column 2, line 5, delete "cydopentane" and insert -- cyclopentane --, therefor.

On the Title page, in Item (57), under "Abstract", in column 2, line 9, delete "cydopentane" and insert -- cyclopentane --, therefor.

In column 1, line 2, delete "ACID,2-CYCLOALKYL" and insert -- ACID, 2-CYCLOALKYL --, therefor.

In column 1, line 26, delete "cydopentane" and insert -- cyclopentane --, therefor.

In column 1, line 27, delete "cydopentane" and insert -- cyclopentane --, therefor.

In column 1, line 31, delete "cydopentane" and insert -- cyclopentane --, therefor.

In column 2, line 20, delete "Fla." and insert -- Fla, --, therefor.

In column 2, line 28, delete "PGE2" and insert -- $PGE_2$ --, therefor.

UNITED STATES PATENT AND TRADEMARK OFFICE
CERTIFICATE OF CORRECTION

PATENT NO. : 6,403,649 B1
APPLICATION NO. : 09/519834
DATED : June 11, 2002
INVENTOR(S) : Woodward et al.

It is certified that error appears in the above-identified patent and that said Letters Patent is hereby corrected as shown below:

In column 2, line 44, after "105" insert -- , --.

In column 3, line 44, delete "akylcarboxy" and insert -- alkylcarboxy --, therefor.

In column 3, line 63, delete "–O(CO)R$^6$" and insert -- –O(CO)R$_6$ --, therefor.

In column 4, line 28, delete "or2" and insert -- or 2 --, therefor.

In column 4, line 43, after "configuration" insert -- . --.

In column 6, line 41, delete "cydopentane" and insert -- cyclopentane --, therefor.

In column 6, line 42, delete "a" and insert -- α --, therefor.

In column 7, line 16, delete "3-αhydroxy" and insert -- 3α-hydroxy --, therefor.

In column 7, lines 16–17, delete "butenyl) 3,5-dihydroxy" and insert
-- butenyl)-3,5-dihydroxy --, therefor.

In column 7, line 18, delete "3-αhydroxy" and insert -- 3α-hydroxy --, therefor.

In column 7, line 23, after "the" delete "a".

In column 7, line 26, delete "5cis" and insert -- 5-cis --, therefor.

In column 7, line 29, delete "cydopentane" and insert -- cyclopentane --, therefor.

In column 7, line 30, delete "5phenyl" and insert -- 5-phenyl --, therefor.

In column 7, line 32, delete "cydopentane" and insert -- cyclopentane --, therefor.

In column 7, line 35, delete "cydopentane" and insert -- cyclopentane --, therefor.

In column 7, line 44, delete "cydopentane" and insert -- cyclopentane --, therefor.

In column 7, line 44, delete "5cis" and insert -- 5-cis --, therefor.

In column 7, line 46, delete "5dihydroxy" and insert -- 5-dihydroxy --, therefor.

In column 7, line 49, delete "5phenyl" and insert -- 5-phenyl --, therefor.

UNITED STATES PATENT AND TRADEMARK OFFICE
CERTIFICATE OF CORRECTION

PATENT NO. : 6,403,649 B1
APPLICATION NO. : 09/519834
DATED : June 11, 2002
INVENTOR(S) : Woodward et al.

It is certified that error appears in the above-identified patent and that said Letters Patent is hereby corrected as shown below:

In column 7, line 51, delete "cydopentane" and insert -- cyclopentane --, therefor.

In column 7, line 52, delete "5 dihydroxy" and insert -- 5-dihydroxy --, therefor.

In column 7, line 60, delete "cydopentane" and insert -- cyclopentane --, therefor.

In column 7, line 63, delete "cydopentane" and insert -- cyclopentane --, therefor.

In column 7, line 64, delete "5phenyl" and insert -- 5-phenyl --, therefor.

In column 7, line 64, delete "pentenyl)3,5" and insert -- pentenyl)-3,5 --, therefor.

In column 7, line 65, after "$5_\alpha$]" insert -- . --.

In column 8, line 61, delete "w/y" and insert -- w/v --, therefor.

In column 9, line 4, delete "w/y" and insert -- w/v --, therefor.

In column 9, line 33, delete "cydopentane" and insert -- cyclopentane --, therefor.

In column 9, line 34, delete "4m-chlorophenoxy" and insert -- 4-m-chlorophenoxy --, therefor.

In column 9, line 34, after "5-dihydroxy" insert -- , --.

In column 9, line 42, delete "2(3$\alpha$" and insert -- 2-(3$\alpha$ --, therefor.

In column 9, line 43, delete "trans butenyl" and insert -- trans-butenyl --, therefor.

In column 9, line 61, delete "cydopentane" and insert -- cyclopentane --, therefor.

In column 10, line 3, delete "dear" and insert -- clear --, therefor.

In column 10, line 7, delete "3$\alpha$-hydroxyl" and insert -- 3$\alpha$-hydroxy --, therefor.

In column 10, line 16, delete "cydopentane" and insert -- cyclopentane --, therefor.

In column 10, line 16, delete "3$\alpha$-hydroxyl" and insert -- 3$\alpha$-hydroxy --, therefor.

In column 10, line 31, delete "25$\mu$:" and insert -- 25$\mu$L --, therefor.

UNITED STATES PATENT AND TRADEMARK OFFICE
CERTIFICATE OF CORRECTION

PATENT NO. : 6,403,649 B1
APPLICATION NO. : 09/519834
DATED : June 11, 2002
INVENTOR(S) : Woodward et al.

It is certified that error appears in the above-identified patent and that said Letters Patent is hereby corrected as shown below:

In column 11, line 48, delete "heat" and insert -- heart --, therefor.

In column 11, line 59, delete "petroatum" and insert -- petrolatum --, therefor.

In column 12, line 30, delete "pyrrplidone" and insert -- pyrrolidone --, therefor.

In column 12, line 48, delete "tables" and insert -- tablets --, therefor.

In column 12, line 57, delete "soribitol" and insert -- sorbitol --, therefor.

In column 13, line 2, after "wherein" insert -- $R_4$ is --.

Signed and Sealed this

Seventh Day of August, 2007

JON W. DUDAS
*Director of the United States Patent and Trademark Office*